United States Patent [19]

Berger et al.

[11] Patent Number: 5,703,015
[45] Date of Patent: *Dec. 30, 1997

US005703015A

[54] PESTICIDAL COMPOSITIONS OF POLYOXYALKYLENE ALKYLAMINE SURFACTANTS HAVING REDUCED EYE IRRITATION

[75] Inventors: Paul D. Berger, Sugar Land; Antonio M. Jimenez, Missouri, both of Tex.

[73] Assignee: Monsanto Company, St. Louis, Mo.

[*] Notice: The term of this patent shall not extend beyond the expiration date of Pat. No. 5,683,958.

[21] Appl. No.: 358,274

[22] Filed: Dec. 19, 1994

Related U.S. Application Data

[63] Continuation-in-part of Ser. No. 101,214, Aug. 4, 1993, abandoned, which is a continuation of Ser. No. 565,816, Aug. 9, 1990, abandoned.

[51] Int. Cl.⁶ ............................................. A01N 57/04
[52] U.S. Cl. .................................................. 504/206
[58] Field of Search .................................... 504/206

[56] References Cited

U.S. PATENT DOCUMENTS

| | | | |
|---|---|---|---|
| 3,117,152 | 1/1964 | Michaels | 260/461 |
| 3,799,758 | 3/1974 | Franz | 504/206 |
| 4,313,847 | 2/1982 | Chasin et al. | 252/356 |
| 4,770,694 | 9/1988 | Iwasaki et al. | 71/93 |
| 4,844,734 | 7/1989 | Iwasaki et al. | 71/120 |
| 4,853,026 | 8/1989 | Frisch et al. | 504/206 |
| 4,912,245 | 3/1990 | Girardeau et al. | 558/113 |
| 4,976,769 | 12/1990 | Iwasaki | 71/86 |
| 5,043,008 | 8/1991 | Iwasaki | 71/86 |
| 5,047,079 | 9/1991 | Djafar et al. | 71/86 |
| 5,078,782 | 1/1992 | Nielsen et al. | 71/100 |
| 5,139,152 | 8/1992 | Hodakowski et al. | 206/524.7 |
| 5,180,414 | 1/1993 | Darchy et al. | 504/206 |
| 5,198,012 | 3/1993 | Iwasaki | 504/344 |

FOREIGN PATENT DOCUMENTS

| | | | |
|---|---|---|---|
| 0255760 | 10/1988 | European Pat. Off. | 25/14 |
| 0290416 | 11/1988 | European Pat. Off. | |
| 2157952 | 11/1985 | United Kingdom | 57/12 |
| 0290416 | 9/1988 | United Kingdom | 25/30 |

*Primary Examiner*—S. Mark Clardy
*Attorney, Agent, or Firm*—Monsanto Company, Arnold, White & Durkee

[57] ABSTRACT

There are provided compositions of certain polyoxyalkylene alkylamine surfactants having eye irritation reduced by the addition of an effective amount of a sulfated polyoxyalkylene alkylphenol, alcohol sulfate, polyoxyalkylene alcohol sulfate, mono- or dialcohol phosphate mono- or di-(polyoxyalkylene alcohol) phosphate, mono-or di-(polyoxyalkylene alkylphenol) phosphate, polyoxyalkylene alkylphenol carboxylate or polyoxyalkylene alcohol carboxylate surfactant. Also provided are pesticidal, particularly herbicidal, compositions comprising polyoxyalkylene alkylamine surfactants having eye irritation reduced by addition of these eye irritation reducing compounds.

9 Claims, No Drawings

PESTICIDAL COMPOSITIONS OF POLYOXYALKYLENE ALKYLAMINE SURFACTANTS HAVING REDUCED EYE IRRITATION

CROSS-REFERENCE TO RELATED APPLICATION

This application is a continuation-in-part application of application Ser. No. 08/101,214 filed Aug. 4, 1993 which is a continuation application of application Ser. No. 07/565, 816 filed Aug. 9, 1990 (now abandoned).

BACKGROUND OF THE INVENTION

The present invention generally relates to novel surfactant compositions, their preparation and to compositions containing these novel surfactant compositions, together with a pesticide, particularly a herbicide. More particularly, an important aspect of this invention is directed to surfactant compositions having reduced eye irritancy which are useful in the preparation of herbicidal compositions having reduced eye irritation properties in addition to their herbicidal effectiveness. In this regard, a further important aspect of the present invention concerns surfactant compositions which are effective in the formulation of glyphosate-containing herbicidal compositions or pesticidal compositions of other water soluble active ingredients. A method of using the herbicidal compositions is also provided.

Numerous organic pesticides; i.e., chemicals that are useful in the control of bacteria, insects, fungi, weeds and the like, have been developed in recent years. These pesticides, especially herbicides, have found use in agriculture, as well as for household applications. Regardless of whether the pesticide is water soluble or water insoluble, it is desirable to use the same in an aqueous medium rather than in a non-aqueous solvent which is more difficult to use by the formulator and applicator, could cause environmental damage, is more costly and is in general less desirable. Water-based dispersions, emulsions and/or solutions can be prepared from most pesticides using selected surfactants. Proper selection of the surfactant can also improve the efficacy of pesticidal compositions.

Surfactants are useful in the preparation of herbicidal compositions whether the herbicide is water soluble or insoluble. When the herbicide is water insoluble, the surfactant can be used to make a water dispersible herbicide composition. When the herbicide is water soluble, the surfactant can often be used to improve the herbicidal effectiveness of the herbicidal composition.

One class of surfactants that has found success in the preparation of herbicidal compositions includes the polyoxyalkylene alkylamines such as, for example, ethoxylated tallowamine. These compounds have the necessary surface activity so that many otherwise water insoluble herbicides, as well as water soluble herbicides, can be formulated into concentrates which will form useful dispersions, emulsions and solutions in water. Herbicides formulated into dispersions, emulsions and solutions using these surfactants often have improved herbicidal properties. This class of surfactants is well known to potentiate the herbicidal activity of glyphosate.

While the polyoxyalkylene alkylamine compounds have excellent surfactant properties which often enhance the efficacy of phytotoxicants, they unfortunately are eye irritants and must be used with a high degree of caution.

Reducing or eliminating the eye irritancy of the polyoxyalkylene alkylamine surfactants used with pesticides, without reducing the efficacy of the pesticidal compositions containing the surfactants, is a highly desirable end. The protection of the applicator and personnel preparing the surfactant and pesticidal compositions from eye damage is of paramount importance. Reducing the eye irritancy of the surfactant and pesticidal compositions containing the surfactant, increases the use that can be made of such products while lessening the possibility of injury to personnel handling and using them.

In order to obtain surfactant compositions having the desired characteristics needed for use with the numerous pesticides on the market, various combinations of surfactants have been previously made.

U.S. Pat. No. 4,313,847 describes three component surfactant compositions including a polyoxyalkylene alkyl or alkylaryl ether phosphate ester, a polyoxyalkylene alkylamine and a material selected from the group consisting of nonionic polyoxylated surfactants, polyhydric alcohol esters and polyoxyalkylene glycols. According to this patent, the three component composition is an improved emulsifier enhancing the use of an emulsion containing a water insoluble herbicide.

Combinations of emulsifiers are also shown in the following patents: U.S. Pat. No. 2,872,368 discloses a polyoxyethylene glycol or a polyoxypropylene glycol in combination with an oil soluble alkaline earth metal salt of an alkylated naphthalene sulfonic acid; U.S. Pat. No. 3,683,078 discloses emulsifier compositions having three components: 1) the condensation product of an alkylphenol and an alkylene oxide, 2) a sulfonate salt and 3) a polyoxyalkylene derivative of an alkanol; and U.S. Pat. No. 3,071,550 discloses selected sulfonates in combination with an aliphatic diester of unsaturated carboxylic acids and the condensation product of glycerin and from about 15 to about 27 moles of ethylene oxide.

As stated in British Patent No. 769,736, due to the diverse nature of pesticides, the selection of the proper emulsifying agent in any particular instance is difficult. This patent shows combinations of a surface active alkylaryl polyoxyalkylene glycol ether and a water soluble salt of a phosphate or sulfate ester as one of the ethers. This British patent, like the preceding patents, shows the continuing need for a multitude of surfactants many of which are obtained by combinations of known materials.

It is known to formulate aqueous solutions of the herbicide glyphosate and sulfated nonalkoxylated $C_8$–$C_{10}$ alkyl alcohol surfactants. Such herbicidal compositions have been sold by Monsanto Company of St. Louis, Mo., for example, under the trademark PONDMASTER.

None of the foregoing patents discusses the problem of surfactants being eye irritants. Yet this is an important factor which must be taken into consideration when preparing and using compositions containing polyoxyalkylene alkylamine surfactants. Thus, there exists an important need for such compositions having reduced eye irritancy without sacrifice of pesticidal activity.

Perhaps the most widely used herbicide worldwide is glyphosate, which chemically is N-phosphonomethylglycine. This product is normally used in an agriculturally acceptable form, such as a water soluble salt; e.g., the isopropylamine salt. For certain commercial uses glyphosate is made into a herbicidal concentrate composition containing a surfactant, which can then be diluted with water for use by the applicator. Often used surfactants for the preparation of these compositions are the aforementioned polyoxyalkylene alkylamines, especially ethoxylated tallowamine. European Patent 290,416 discloses combinations of solubilized glyphosate, equivalent to at least 40 grams per liter of glyphosate acid, and alkoxylated alkylamine surfactants in a ratio of the solubilized glyphosate (expressed as glyphosate acid equivalent) to amine surfactant of from about 1:1.75 to about 6:1. According to this European Patent, the compositions permit a reduction in the surfactant to glyphosate ratio without loss of herbicidal effectiveness. Clearly, the use of compositions containing glyphosate and alkoxylated tallowamine having reduced eye irritation is of considerable importance. The invention described herein presents a method of improving the highly desirable properties of such compositions.

The U.S. Environmental Protection Agency requires that currently commercial aqueous concentrate glyphosate herbicide solutions having an alkoxylated alkylamine surfactant be labelled to contain a precautionary statement that the solution can cause eye burns. To remedy or ameliorate this hazard is a desideratum of long standing.

It is therefore an object of the present invention to provide new compositions containing an alkoxylated alkylamine surfactant.

Another object of the present invention is to provide such surfactant-containing compositions that can be used to prepare pesticidal compositions, particularly herbicidal compositions having significantly reduced eye irritancy.

Another object of the present invention is to provide new methods for the preparation of compositions containing an alkoxylated alkylamine surfactant and having reduced eye irritancy.

Another object of the present invention is to provide compositions of the herbicide glyphosate having agriculturally acceptable herbicidal efficacy and reduced eye irritancy.

Another object of the present invention is to provide new methods for controlling the growth of weeds and other vegetation.

Other objects of the present invention will become apparent from the following description.

SUMMARY OF THE INVENTION

The present invention is directed to a surfactant composition 0comprising a polyoxyalkylene alkylamine having at least about 2 moles of an alkylene oxide group and reduced eye irritancy. An important embodiment of this invention is a surfactant composition comprising a polyoxyalkylene alkylamine contiaing at least about 2 moles of an alkylene oxide group and any of a range of eye irritation reducing compounds, such as sulfated polyoxyalkylene alkylphenol; alcohol sulfates; polyoxyalkylene alcohol sulfates; mono- and dialcohol phosphates; mono- and di- (polyoxyalkylene alcohol) phosphates; mono- and di- (polyoxyalkylene alkylphenol) phosphates; polyoxyalkylene alkylphenol carboxylates or polyoxyalkylene alcohol carboxylates, said eye irritation reducing compounds containing up to about 60 moles of an alkylene oxide group and alkyl and alcohol groups having from about 8 to about 20 carbon atoms.

A glycol can be present in the surfactant composition in order to improve the solubility of the surfactant composition. The glycol can be formed in situ during the preparation of the polyoxyalkylene alkylamine, or the glycol can be added to the amine or the surfactant composition.

Also the present invention contemplates pesticidal compositions, particularly herbicidal compositions, comprising a pesticide such as a herbicide and the aforedescribed surfactant composition. These compositions are readily dispersible in water so as to prepare aqueous compositions useful for the control of weeds, insects, fungi and the like.

In accordance with a preferred embodiment of the present invention an aqueous solution is provided which comprises a herbicidally effective amount of a glyphosate herbicide, either in the acid or salt form, whose herbicidal effectiveness is enhanced by the presence of a potentiating effective amount of a oxyalkylene alkylamine surfactant, and whose eye irritancy caused by the presence of said alkylamine surfactant in the solution is reduced by incorporating an eye irritation reducing amount of an anionic surfactant.

DETAILED DESCRIPTION OF THE INVENTION

The surfactant compositions of the present invention comprise a polyoxyalkylene alkylamine having at least about 2 moles of an alkylene group, said surfactant composition having an eye irritancy lower than the eye irritancy of said polyoxyalkylene alkylamine.

One method for reducing the eye irritancy of the polyoxyalkylene alkylamine is to blend it with an effective amount of an eye irritation reducing compound. Examples of compounds useful for this purpose are sulfated polyoxyalkylene alkylphenol; alcohol sulfates; polyoxyalkylene alcohol sulfates; mono- and dialcohol phosphates; mono- and di- (polyoxyalkylene alcohol) phosphates; mono- and di- (polyoxyalkylene alkylphenol) phosphates; polyoxyalkylene alkylphenol carboxylates or polyoxyalkylene alcohol carboxylates, said eye irritation reducing compounds containing up to about 60 moles of an alkylene oxide group and alkyl and alcohol groups having from about 8 to about 20 carbon atoms.

The present invention more specifically provides an aqueous or water soluble composition comprising one or more salts of glyphosate in a herbicidally effective amount. The composition contains an amine surfactant having the chemical structure

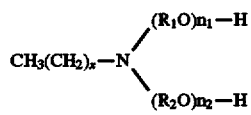

wherein x is a number from 7 to about 19, $n_1$ and $n_2$ are numbers independently selected from 1 to about 30, the average sum of $n_1$ and $n_2$ is greater than 2, and $R^1$ and $R_2$ are $C_2$–$C_4$ alkylene radicals. The amine surfactant is present in an amount sufficient to potentiate the glyphosate herbicidal activity. Also present in the composition is an acidic compound having the chemical structure

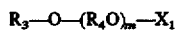

wherein $R_3$ is $C_8$–$C_{20}$ alkyl or $C_8$–$C_{20}$ alkylphenyl, $R_4$ is a $C_2$–$C_4$ alkylene radical, m is a number from 0 to about 60, and $X_1$ is selected from the group consisting of carboxylate, sulfate and phosphate radicals. The acidic compound is present in a sufficient amount to reduce the eye irritancy of the composition caused by the presence of the amine surfactant component to an acceptable level.

The present invention is directed to a surfactant composition comprising a polyoxyalkylene $C_8$–$C_{20}$ alkylamine surfactant having at least about 2–4 moles of a $C_2$–$C_4$ alkylene oxide group and reduced eye irritancy. An important embodiment of this invention is a surfactant composition comprising a polyoxyalkylene alkylamine surfactant containing at least about 2–4 moles of an alkylene oxide group and an effective amount of at least one eye irritation reducing compound, such as sulfated polyoxyalkylene alkylphenol; alcohol sulfates; polyoxyalkylene alcohol sulfates; mono- and dialcohol phosphates; mono- and di-(polyoxyalkylene alcohol) phosphates; mono- and di-(polyoxyalkylene alkylphenol) phosphates; polyoxyalkylene alkylphenol carboxylates or polyoxyalkylene alcohol carboxylates, said eye irritation reducing compounds containing up to about 60 moles of a $C_2$–$C_4$ alkylene oxide group and alkyl and alcohol groups having from about 8 to about 20 carbon atoms.

A glycol and/or polyalkylene glycol can be present in the surfactant composition in order to improve the water solubility of the surfactant composition and to suppress gelation of the surfactant composition in concentrated form. The glycol or polyglycol can be formed in situ during the preparation of the polyoxyalkylene alkylamine, or the glycol or polymeric glycol can be added to the amine or the surfactant composition.

Also, the present invention contemplates pesticidal compositions, particularly herbicidal compositions, comprising a pesticide, such as a herbicide and the aforedescribed surfactant composition having reduced eye irritancy. These compositions are readily dispersible or soluble in water so as to prepare aqueous-based compositions useful for the control of weeds, insects, fungi and the like.

In soaps, detergents and abrasives used for cleansing the skin on various portions of the body, anionic surfactants when used in such compositions are known to be adsorbed and thereby remain on the skin surface to cause dryness and scaling of the epidermis, or skin chapping and roughness.

With the alkoxylated alkylamine surfactants known to cause eye irritation in glyphosate-containing aqueous solutions and with the just discussed known drawbacks of anionic surfactants on skin, it is surprising and unexpected that the addition of an effective amount of anionic surfactants to the aqueous solutions of alkoxylated alkylamine surfactant would ameliorate the eye irritation thereof.

In accordance with the present invention, one method for reducing the eye irritancy of the polyoxyalkylene alkylamine is to blend such amine with an effective amount of an eye irritation reducing compound. Examples of compounds useful for this purpose are sulfated polyoxyalkylene alkylphenol; alcohol sulfates and polyoxyalkylene alcohol sulfates; mono- and dialcohol phosphates; mono- and di-(polyoxyalkylene alcohol) phosphates; mono- and di-(polyoxyalkylene alkylphenol) phosphates; polyoxyalkylene alkylphenol carboxylates and polyoxyalkylene alcohol carboxylates, including mixtures thereof, said eye irritation reducing compound containing up to about 60 moles of an alkylene oxide group and alkyl and alcohol groups having from about 8 to about 20 carbon atoms.

In many but not all embodiments of the present invention, both components of the surfactant composition are polyoxyalkylene derivatives. Such materials are often referred to as an alkoxylated product or an alkylene oxide product. Often these alkylene oxide products are mixtures of compounds containing different numbers of alkylene oxide groups, of which one may predominate, being accompanied by smaller proportions of products containing larger and smaller numbers of the alkylene oxide groups in the polyoxyalkylene portion of the molecule.

The polyoxyalkylene alkylamine surfactants are commercially available materials, being used as surfactants for the preparation of pesticidal compositions, particularly herbicidal compositions wherein the alkylamine enhances the activity of the herbicide. Glyphosate is one example where the alkylamines notably enhance or potentiate the herbicidal activity thereof. These amine surfactants can be prepared by reacting under suitable conditions, preferably in the presence of a catalyst, an alkylene oxide, preferably ethylene and/or propylene oxide with a long chain alkylamine, preferably an alkylamine containing from about 8 to about 20 carbon atoms. The oxyalkylated moiety can be a random or block copolymer of ethylene and propylene oxide units. These $C_8$–$C_{20}$ alkyl primary amines may be derived from naturally occurring products such as tallow, coconut, soybean or cotton seed oils and as such are mixtures of amines. A preferred amine is tallowamine. The polyoxyalkylene derivatives thereof are prepared by reacting alkylene oxide with the selected alkylamine at elevated temperatures and pressure. Procedures for carrying out these reactions are known to those skilled in the art.

A generalized structural representation of the polyoxyalkylene alkylamines is depicted as follows:

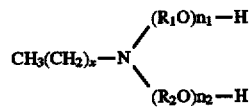

wherein x is a number from about 7 to about 19; $n_1$ and $n_2$ are numbers independently selected from 1 to about 30, and the average sum of $n_1$ and $n_2$ is 2 or greater and may be as high as 60; and $R_1$ and $R_2$ are independently selected from lower alkylene, having from 2 to about 4 carbon atoms, preferably 2 carbon atoms. The amount of alkylamine surfactant will be sufficient to potentiate the activity of the selected pesticide.

The amount of alkylene oxide used in the preparation of this component of the surfactant composition varies with the ultimate use of the surfactant composition. Normally, up to about 60 moles of oxyalkylene groups in the polyoxyalkylene alkylamine are satisfactory, with from about 4 to about 20 moles being preferred, and from about 8 to about 13 moles of oxyalkylene groups being most preferred.

Sulfated polyoxyalkylene alkylphenols can be prepared by first alkoxylating an alkylphenol and then reacting the alkoxylated alkylphenol with a suitable quantity of sulfur trioxide. One procedure for such preparation is to contact a mixture of air and sulfur trioxide with the selected alkoxylated alkylphenol in a falling film reactor. Other procedures that may be used include reactions with oleum or with chlorosulfonic acid. This reaction will cause the formation of sulfate groups as a terminal group on the alkoxylated portion of the molecule and often some sulfonate groups substituted on the phenyl moiety. The preparation of the sulfated polyoxyalkylene alkylphenol can produce product having from 0 to 30 or more weight percent of the sulfated polyoxyalkylene alkylphenol having sulfonate groups on the phenyl moiety. For many purposes it is preferred that at least about 3 weight percent of the sulfated polyoxyalkylene alkyl phenol be sulfonated.

In the acid form the sulfated polyoxyalkylene alkylphenols are inherently unstable under normal conditions. The adverse affects of such instability can be avoided by mixing the sulfated polyoxyalkylene alkylphenols shortly after their production with the alkylamine surfactant. The mixing results in the formation of a stable salt of the two components. If it is desired to mix the two components at a time significantly later than the production of the sulfated polyoxyalkylene alkylphenol, a stable composition can be made and can be stored for some time before mixing. For example, alkali metal salts and amine salts of the sulfated polyoxyalkylene alkylphenol surfactants are more stable as compared to such surfactants in acid form.

A generalized structural representation of the predominant component of the sulfated polyoxyalkylene alkylphenol optionally containing ring sulfonation is as follows:

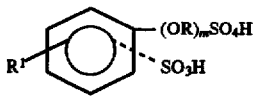

wherein m is a number up to about 60, preferably less than 10 and more preferably about 4, R is alkylene having from 2 to about 4 carbon atoms, preferably 2, and $R^1$ is alkyl having about 8 to about 20 carbon atoms, preferably 9–15 carbon atoms. The amount of sulfated polyoxyalkylene alkylphenol compound in the composition should be sufficient to reduce the eye irritation of the alkylamine surfactant. It is preferred that at least 3% of the sulfated polyoxyalkylene alkylphenol compound be ring sulfonated. The broken line in the above formula indicates that the ring sulfonation is optional and, if sulfonated, the sulfonate substituent normally is in the meta or ortho position with respect to $R^1$. Eye irritation reduction can be obtained without the compound having been ring sulfonated.

The amount of alkylene oxide used in the preparation of this component of the surfactant composition varies with the ultimate use of the surfactant composition. Normally, there can be up to about 30 or more moles of alkylene oxide in the sulfated polyoxyalkylene alkylphenol. For certain agricultural applications it is preferred to have from about 4 to about 14 or more moles of the alkylene oxide units. For specific uses it is preferred that there be present less than 10 moles of alkylene oxide groups and preferably about 4 moles of alkylene oxide groups, most preferably about 4 moles of ethylene oxide in the sulfated polyoxyalkylene alkylphenol having at least 3% sulfonation.

The alkyl group in the alkylphenol moiety can comprise from about 8 to about 20 carbon atoms. A preferred alkyl is nonyl due to the availability and properties of surfactants having this moiety. It should be understood that for specific applications, alkylphenol moieties containing more or fewer carbon atoms can be used.

In order to obtain the desired results, of the total sulfated polyoxyalkylene alkylphenol preferably at least about 3 weight percent have sulfonate substituents. The sulfonated component can comprise up to 30 weight percent or more of the total alkylphenol. For certain applications the sulfated polyoxyalkylene compounds of which about 15 weight percent have sulfonate substituents can be effectively used in the present surfactant compositions.

Other eye irritant reducing compounds can also be used to reduce the eye irritancy of the polyoxyalkylene alkylamines. Alcohol sulfates and polyoxyalkylene alcohol sulfates having from about 8 to 18 carbon atoms and up to about 12 moles of alkoxyalkylene group are particularly useful. As with the sulfated polyoxyalkylene alkylphenol and the polyoxyalkylene alkylamines, it is preferred that the alkylene oxide groups in the polyoxyalkylene alcohol sulfates be ethylene oxide groups. Oxyalkylene groups from 2 to about 4 carbon atoms are often used. While there can be 30 or more moles of an oxyalkylene group in the polyoxyalkylene alcohol sulfate, polyoxyalkylene alcohol sulfate preferably contains about 3 moles of alkylene oxide groups, preferably 3 moles of ethylene oxide groups.

Mono- and dialcohol phosphates; mono- and di-(polyoxyalkylene alcohol) phosphates; mono- and di-(polyoxyalkylene alkylphenol) phosphates; polyoxyalkylene alkylphenol carboxylates and polyoxyalkylene alcohol carboxylates are additional eye irritant reducing compounds that can be used to reduce the eye irritancy of the polyoxyalkylene alkylamines.

These compounds can contain from about 8 to about 20 carbon atoms in their alkyl and alcohol groups and up to about 30 moles of alkylene oxide, preferably ethylene oxide, in each polyoxyalkylene alcohol or polyoxyalkylene alkylphenol group. As with the sulfated polyoxyalkylene alkylphenol, it is preferred that the polyoxyalkylene alkylphenol phosphates and carboxylates be polyoxyethylene nonylphenol phosphates and polyoxyethylene nonylphenol carboxylates.

These carboxylate and phosphate components are available materials which can be readily prepared by methods known in the art. As one example of such a procedure, the phosphates can be obtained by reacting a suitable polyoxyalkylene alkylphenol with phosphorus pentoxide or polyphosphoric acid. The selection of the exact components and their amounts depends on the identification of the desired phosphate. By varying the components used in the preparation of the phosphate, it is possible to maximize the presence of mono- or diester. Often the phosphates are mixtures of the mono- and diesters. The preference for the mono- or diester of phosphoric acid depends upon variables such as the ultimate use of the surfactant composition, the identity of the pesticide, the intended use of the pesticide composition and other factors. U.S. Pat. No. 4,313,847 describes the preparation of the phosphates.

The mono- and dialcohol phosphates, mono- and di-(polyoxyalkylene alcohol) phosphates and the mono- and dialcohol phosphates, (polyoxyalkylene alkylphenol) phosphates useful in accordance with the present invention are represented by the following general formula

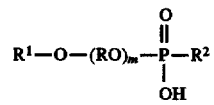

wherein $R^1$ is $C_8$–$C_{20}$ alkyl or $C_8$–$C_{20}$ alkylphenyl; R is an alkylene having from 2 to about 4 carbon atoms, usually ethylene or propylene, m is zero or a number up to about 60, preferably less than 10 and more preferably about 4, and $R^2$ is hydroxyl or the $R^1$—O—$(RO)_m$-radical wherein $R^1$, R, and m are as just indicated. If $R^2$ is hydroxyl, then the compound is a monoester. If $R^2$ is a $R^1$—O—$(RO)_m$-radical, then the compound is a diester. Mixtures of monoesters and diesters are also useful, together with the polyoxyalkylene alkylamines.

Certain of the eye irritant reducing components of the present surfactant compositions are commercial materials. For example, nonylphenol phosphate containing 4 moles of ethylene oxide, $C_8$–$C_{10}$ alcohol phosphates and sulfated nonylphenol containing 4 moles of ethylene oxide have been marketed by Witco Corp. under the names EMPHOS CS-121, EMPHOS PS-400, and WITCONATE D-51-29, respectively. (EMPHOS and WITCONATE are trademarks of Witco Corp.)

More particularly, the phosphate mono-esters of polyoxyethylene alkylphenol and the phosphate di-esters of the polyoxyethylene alkylphenol useful for reducing the eye irritancy of the selected polyoxyalkylene alkylamine surfactant in accordance with the present invention, respectively, have the following chemical structures.

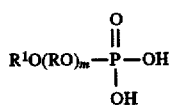

Mono-ester

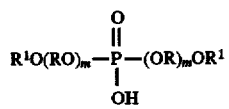

Di-ester wherein m is zero or a number up to about 60, preferably 9–15, R is $C_2$–$C_4$ alkylene, preferably ethylene and $R^1$ is $C_8$–$C_{20}$ alkyl or $C_8$–$C_{20}$ alkylphenyl. The amount of phosphate compound in the composition should be sufficient to reduce the eye irritation of the polyoxyethylene alkylamine surfactant. Mixtures of monoester and diester are also useful. Normally, the diester to the mono-ester is present in a weight ratio of 5:95 to 50:50.

In general the surfactant composition comprises a major amount of polyoxyalkylene alkylamine component and an effective amount of the selected eye irritation reducing compound. The eye irritation reducing compound is present in the surfactant composition in an effective amount sufficient to reduce the eye irritation properties of the polyoxyalkylene alkylamine. When the eye irritation reducing compound is a sulfated polyoxyalkylene alkylphenol, preferred surfactant compositions can contain from about 50 to about 95 weight percent, preferably about 80 to about 85 weight percent, of the polyoxyalkylene alkylamine and from about 5 to about 50 weight percent of the eye irritation reducing component. The optimum amount of each component in the surfactant blend depends on variables such as the identity of the eye irritation reducing compound, the identity of the pesticide, the type of application of the pesticide composition, storage and transportation of the surfactant and pesticide compositions, the conditions of use of the pesticidal compositions, etc. When a water soluble salt of glyphosate is the pesticide and sulfated polyoxyalkylene alkylphenol is the eye irritation reducing component, it has been found desirable to use a composition which comprises about 85 weight percent of the polyoxyalkylene alkylamine and about 15% by weight of the sulfated polyoxyalkylene alkylphenol. Other ratios may also be useful.

The surfactant composition of the present invention can contain optional components to improve the water solubility of the surfactant composition and suppress gel formation. The need for such components will depend upon several factors, especially the identity of the surfactants comprising the composition. Among compounds useful for improving the water solubility of the surfactant composition are glycols and polyglycols. Glycols are of particular use for this function due to their solubility in water. The readily available glycols, ethylene glycol, propylene glycol, polyethylene glycol and polypropylene glycol are satisfactory for this function although other glycols can also be used. Other organic compounds with high water solubility will also be useful in certain instances. The antigelation additive preferably is polyethylene glycol having an average molecular weight of about 200 to about 1000.

While the glycol can be added to the surfactant composition with mixing, its use therein is independent of the method of its introduction into the surfactant composition. Thus, for example, it can be introduced into the surfactant composition with the polyoxyalkylene alkylamine component. This is often a preferred method since the glycol and/or polymeric glycol can be made during the manufacture of the polyoxyalkylene alkylamine component as a byproduct of the alkoxylation reaction. Other procedures for obtaining and introducing the optional glycol component can be used.

Most of the individual components discussed above are liquids at room temperatures. However, in the case of those materials containing a large polyoxyalkylene chain, some of the materials may be waxy at room temperature and if this is the case, the materials can be heated to liquefy the same prior to mixing. The surfactant compositions of the present invention can be prepared by blending the components in a conventional manner. Any suitable equipment, such as a conventional mixer, may be used. The order of adding the materials to the composition generally is not critical and thus they may be blended in any convenient order. As mentioned above, the amounts of the individual components utilized can be varied somewhat depending upon a variety of factors, particularly the ultimate application of the composition.

Surfactant compositions of the present invention are especially useful in the preparation of pesticidal compositions designed to be delivered by spraying, particularly sprayable herbicidal compositions. The term "pesticide" includes chemicals and microbial agents used as active ingredients of products for control of crop and lawn pests and diseases, animal ectoparasites, and other pests in public health. The term also includes plant growth regulators, pest repellants, synergists, herbicide safeners (which reduce the phytotoxicity of herbicides to crop plants) and preservatives, the delivery of which to the target may expose dermal and especially ocular tissue to the pesticide. Such exposure can arise by drift of the pesticide from the delivery means to the person performing the application of the pesticide or being present in the vicinity of an application.

In general, a herbicidal composition known as a concentrate is first prepared. This composition in essence contains a herbicide and a surfactant mixture. Often it includes a minor amount of solvent, such as water. Alternatively, the concentrate composition may be in dry form with or without an inert solid carrier, for example, as a water soluble or water dispensible granular formulation. The ratio of herbicide to surfactant will depend on many factors, including but not limited to the identity of the components and the ultimate use. Usually the surfactant will comprise from about 5 to about 25 weight percent of this composition. The concentrate can then be diluted with water to form an aqueous herbicidal composition ready for use by spraying. The present herbicidal compositions are not limited to a particular herbicide or mixture of herbicides. They may be used with a variety of pesticides, including but not limited to herbicides in any of their water soluble salt forms. Among such herbicides are glyphosate and acifluorfen (5-(2-chloro-4-(trifluoromethyl)phenoxy)-2-nitrobenzoic acid), chloramben (3-amino-2,5-dichlorobenzoic acid), 2,4-D ((2,4-dichlorophenoxy) acetic acid), endothal (7-oxabicyclo (2.2.1)heptane-2,3-dicarboxylic acid), mecoprop (2-(2-methyl-4-chlorophenoxy) propionic acid), picloram (4-amino-3,5,6-trichloropyridine-2-carboxylic acid), 2,4,5-T((2,4,5-trichlorophenoxy)acetic acid), benzac (2,3,6-trichlorobenzoic acid), dicamba (3,6-dichloro-o-anisic acid), MCPA (4-chloro-o-tolyloxyacetic acid), dalapon (2,2-dichloropropionic acid), dichlorprop (2-(2,4-dichlorophenoxy)propionic acid), MCPB (4-(4-chloro-o-tolyloxy)butyric acid), bialaphos (L-2-amino-4-((hydroxy) (methyl)phosphinoyl)butyryl-L-alanyl-L-alanine), glufosinate ((3-amino-3-carboxypropyl) methylphosphinate), imazethapyr (2-[4,5-dihydro-4-methyl- 4-(1-methylethyl)-5-oxo-1H-imidazol-2-yl]-5-ethyl-3-pyridinecarboxylic acid), imazaquin (2-[4,5-dihydro-4-methyl-4-(1-methylethyl)-5-oxo-1H-imidazol-2-yl]-3-quinolinecarboxylic acid), mixtures thereof and the like. Preferred results, however, are obtained with the herbicide glyphosate whose activity is derived from N-phosphonomethylglycine. Glyphosate is normally formulated from water soluble salts thereof. U.S. Pat. No. 3,853,530 discloses the use of glyphosate and its derivatives as herbicides.

Since glyphosate in acid form has limited water solubility (about 1.2%) the water soluble salts of glyphosate are normally used for most applications. Among the water soluble salts of glyphosate are the trimethylsulfonium salt, the ammonium salt, the isopropylamine salt, and the alkali metal salts, such as sodium and potassium. These compounds due to their solubility in water are the agriculturally acceptable glyphosate-containing compounds generally used in commerce.

It is known to use mixtures of glyphosate and one or more of its water soluble salts. Previously mentioned European Patent 290,416 discloses the use of such mixtures which have the advantage of a higher concentration of glyphosate in the final product. However, the low solubility of the glyphosate in acid form limits the amount of it in the total composition. This amount will depend in general on the solubility of the water soluble salt used in the combination.

The pesticidal compositions previously described can be diluted with water to form an aqueous pesticidal composition which can be sprayed or otherwise applied to the desired area. Glyphosate-based herbicides are applied to the foliage of the vegetation to be controlled.

The relative amounts of herbicide, water and surfactant in the aqueous herbicidal compositions of this invention will vary depending upon many factors including but not limited to the identity and properties of the herbicide, method of application, locus to which the herbicide is applied, etc.

The weight ratio of glyphosate expressed as acid equivalent to surfactant composition is normally in the range of 1:1 to 5:1.

Stable aqueous concentrate compositions of the present invention can be made with glyphosate salts at a concentration from about 5% to about 50%, preferably about 35% to about 45%, surfactant composition at a concentration of about 5% to about 25%, preferably about 10% to about 15%, and water making up the balance to 100%. Dry water soluble granular (WSG) or water dispersible granular (WDG) compositions of the present invention can be made with glyphosate salts at a concentration from about 10% to about 85%, preferably about 50% to about 80%, surfactant composition at a concentration of about 5% to about 30%, preferably about 10% to about 25%, and optionally inert ingredients making up the balance to 100%. All percentages above are understood as being by weight.

It is to be noted that in accordance with the preferred practice of the present invention, a multicomponent surfactant composition is provided. One component is a polyoxyalkylene alkylamine surfactant as defined above. A second component present in an eye irritancy reducing amount is an anionic sulfated polyoxyalkylene alkylphenol surfactant having the following chemical structure which preferably contains a minor amount of ring sulfonation.

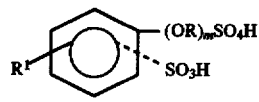

wherein $R^1$, R and m are defined as above. In other words, of the total polyoxyalkylene alkylphenol in the surfactant composition the mole percent of phenol compound having a sulfonate substituent to phenol compound having no sulfonate substituent is preferably in the range of 3–50. The amount of the second component is an amount sufficient to result in an effective reduction of tissue irritation due to the presence of the amine surfactant component in the surfactant composition. The —$SO_3H$ substituent on the phenyl moiety and $R^1$ are normally separated by one ring carbon.

It is also to be noted that in accordance with another preferred practice of the present invention, a multicomponent surfactant composition is provided wherein one component is a cationic polyoxyalkylene alkylamine surfactant as defined above and wherein a second component present in an eye irritation reducing amount is a phosphate ester having one or both of the following chemical structures:

wherein m is zero or a number up to about 60, preferably 9–15, R is $C_2$–$C_4$ alkylene, preferably ethylene and $R^1$ is $C_8$–$C_{20}$ alkyl or $C_8$–$C_{20}$ alkylphenyl.

The surfactant composition of the present invention is normally soluble in water and thus can be used in a water based formulation or water soluble dry formulation for delivering such as by spraying a pesticidally effective amount of the selected pesticide to the point of desired application.

In one preferred embodiment of the present invention the surfactant composition comprised of the amine surfactant component and the sulfated polyoxyalkylene alkylphenol having sulfonate substituents in the phenyl moiety and/or phosphate ester as above defined can effectively be used to formulate glyphosate. Glyphosate is the widely recognized common name for N-phosphonomethylglycine, the biologically active entity of which is the acid form and may be used in the form of an ester but is normally used in the form of water soluble salts. Water soluble salts include alkali metal salts of glyphosate, and organic salts of glyphosate including onium salts such as ammonium, sulfonium and phosphonium salts of glyphosate. The most preferred salts include ammonium, isopropylammonium and trimethylsulfonium salts of glyphosate.

The surfactant composition of the present invention, in addition to the amine surfactant component and the anionic eye irritation reducing surfactant component, may contain about 1–10 weight percent polyalkylene glycol, preferably polyethylene glycol (PEG) having a molecular weight of about 200–1000 to increase the water solubility of the two other components. Instead of or in addition to the polyethylene glycol (PEG), one may include in the surfactant composition of the present invention ethylene glycol and propylene glycol to further increase the water solubility of the amine surfactant component and the eye irritation reducing component, if desired.

These following examples represent compositions tested to demonstrate the unexpectedly mild eye irritation properties provided by the present invention. All compositions contained the monoisopropylamine salt of glyphosate as the herbicide. Tables 1 and 2 contain the results of these tests. The following test procedure was used in these experiments.

These examples were performed in accordance with Pesticidal Assessment Guidelines, Subdivision F, Hazard Evaluation: Human and Domestic Animals, U.S. Environmental Protection Agency (EPA) Publication, EPA 540/9-84-014, November, 1984. Studies were conducted in compliance with EPA Good Laboratory Practice Standards (Federal Register, Vol. 48, Nov. 29, 1983).

Unless otherwise indicated in each of the following examples, an aqueous solution of the isopropylamine salt of glyphosate containing 61.3 weight percent of such glyphosate salt was used as the herbicidal component and is referred to as "glyphosate solution". A mixture of about 70 weight percent polyoxyethylene tallowamine containing from about 8 to 13 moles of ethylene oxide groups and about 30 weight percent polyethylene glycol (MW=600) which may be abbreviated as PEG-600 was used as a component of the surfactant composition and is referred to as "ethoxylated tallowamine" or abbreviated as "ETA".

All parts and percentages in the following examples are given on a weight to weight basis unless otherwise indicated.

Examples 1 and 2 are experiments performed with a glyphosate composition containing ethoxylated tallowamine as its only surfactant component.

EXAMPLE 1

Example 1 was performed with a test material prepared by mixing glyphosate solution (69.3 grams), ethoxylated tallowamine (13.0 grams) and water (17.7 grams).

EXAMPLE 2

Example 2 was performed with a test material prepared by mixing glyphosate solution (69.3 grams), ethoxylated tallowamine (15.4 grams) and water (15.3 grams).

Examples 3–13 are experiments performed with a surfactant composition containing ethoxylated tallowamine and a sulfated ethoxylated nonylphenol.

EXAMPLE 3

Example 3 was performed with a test material prepared by mixing glyphosate solution (69.3 grams); water (15.3 grams) and surfactant composition (15.4 grams) having a pH of 7.5 and containing ethoxylated tallowamine (13.1 grams) and sulfated polyoxyethylene nonylphenol (2.2 grams) having 4 moles of ethylene oxide groups and about 3 weight percent sulfonate.

EXAMPLE 4

Example 4 was performed with a test material prepared by mixing glyphosate solution (69.3 grams); water (15.2 grams) and surfactant composition (15.4 grams) containing ethoxylated tallowamine (13.5 grams) and sulfated polyoxyethylene nonylphenol (1.9 grams) having 2 moles of ethylene oxide groups and about 6 weight percent sulfonate.

EXAMPLE 5

Example 5 was performed with a test material prepared by mixing glyphosate solution (69.3 grams), water (15.3 grams) and surfactant composition (15.4 grams) containing ethoxylated tallowamine (13.5 grams) and sulfated polyoxyethylene nonylphenol (1.9 grams) having 2 moles of ethylene oxide groups and about 15 weight percent sulfonate.

EXAMPLE 6

Example 6 was performed with a test material prepared by mixing glyphosate solution (2.94 grams), water (96.39) grams and surfactant composition (0.67 grams) containing JETCO ethoxylated tallowamine (0.57 grams) and sulfated polyethoxyethylene nonylphenol (0.10 grams) having 4 moles of ethylene oxide groups and about 6 weight percent sulfonate.

EXAMPLE 7

Example 7 was prepared by mixing glyphosate solution (2.94 grams), water (96.39 grams) and surfactant composition (0.67 grams) containing ARMAK ethoxylated tallowamine (0.57 grams) and sulfated polyoxyethylene nonylphenol (0.10 grams) having 4 moles of ethylene oxide groups and about 6 weight percent sulfonate.

EXAMPLE 8

Example 8 was prepared by mixing glyphosate solution (69.3 grams), water (15.3 grams) and surfactant composition (15.4 grams) containing ethoxylated tallowamine (13.1 grams) and sulfated polyoxyethylene nonylphenol (2.3 grams) having 4 moles of ethylene oxide groups and about 6 weight percent sulfonate.

EXAMPLE 9

Example 9 was prepared by mixing glyphosate solution (69.3 grams), water (15.3 grams) and surfactant composition (15.4 grams) containing ethoxylated tallowamine (13.1 grams) and sulfated polyoxyethylene nonylphenol (2.3 grams) having 4 moles of ethylene oxide and about 13 weight percent sulfonate.

EXAMPLE 10

Example 10 was prepared by mixing a glyphosate solution (69.3 grams), water (15.3 grams) and a surfactant composition (15.4 grams) having a pH of 6.5 containing ethoxylated tallowamine (13.1 grams) and sulfated polyoxyethylene nonylphenol (2.3 grams) having 4 moles of ethylene oxide and about 85 weight percent sulfonate.

EXAMPLE 11

Example 11 was prepared by mixing a glyphosate solution (69.3 grams), water (15.3 grams) and a surfactant composition (15.4 grams) having a pH of 7.1 containing ethoxylated tallowamine (13.8 grams) sulfated polyoxyethylene nonylphenol (1.5 grams) having with 4 moles of ethylene oxide and about 85 weight percent sulfonate.

EXAMPLE 12

Example 12 was prepared by mixing a glyphosate solution (69.3 grams), water (15.3 grams) and a surfactant composition (15.4 grams) having a pH of 7 containing ethoxylated tallowamine (13.1 grams) and sulfated polyoxyethylene nonylphenol (2.3 grams) having 10 moles of ethylene oxide groups and about 6 weight percent sulfonate.

EXAMPLE 13

Example 13 was prepared by mixing a glyphosate solution (69.3 grams), water (15.3 grams) and a surfactant composition (15.4 grams) containing ethoxylated tallowamine (11.9 grams) and sulfated polyoxyethylene nonylphenol (3.5 grams) having 10 moles of ethylene oxide groups and about 6 weight percent sulfonate.

Examples 14 and 15 are experiments performed with a surfactant composition containing ethoxylated tallowamine and an alcohol sulfate.

EXAMPLE 14

Example 14 was prepared by mixing a glyphosate solution (69.3 grams), water (15.3 grams) and a surfactant composition (15.4 grams) containing ethoxylated tallowamine (13.1 grams) and alcohol sulfate (2.3 grams) from a mixture of alcohols having from 8 to 10 straight chain carbon atoms.

EXAMPLE 15

Example 15 was prepared by mixing a glyphosate solution (69.3 grams), water (15.3 grams) and a surfactant composition (15.4 grams) containing ethoxylated tallowamine (13.9 grams) and alcohol sulfate (1.5 grams) from a mixture of alcohols having from 8 to 10 carbon atoms.

In Tables 1 and 2 below data are provided showing the average eye irritation of six rabbits exposed in individual tests to each of the compositions of Examples 1–15 using the EPA test referenced above. The data in Table 1 were obtained where the composition was not washed out of the eyes. The data in Table 2 were obtained where the composition was washed out of the rabbits' eyes after being applied to the eyes. Observations are made after 1 hour, 1 day, 2 days, etc. after initial instillation. The average score is an indication of the eye irritation potential of the composition under test.

TABLE 1

Average Irritation Scores (Non-Washed Eyes)

| EXAM-PLE | DAYS AFTER TREATMENT | | | | | | | | | |
|---|---|---|---|---|---|---|---|---|---|---|
| | 1 hr | 1 | 2 | 3 | 4 | 7 | 10 | 14 | 17 | 21 |
| 1 | 18.0 | 15.2 | 19.0 | 14.0 | 11.8 | 10.5 | 7.0 | 5.3 | 3.8 | 4.0 |
| 2 | 20.7 | 19.3 | 17.2 | 15.3 | 12.3 | 4.7 | 6.3 | 6.5 | 5 | 3.5 |
| 3 | 17.2 | 10.2 | 10.8 | 9.2 | 7.6 | 6.4 | 6.4 | 9.5 | 6.5 | 9 |
| 4 | 15.3 | 21.2 | 13 | 9.2 | 8.2 | 5.3 | 4.3 | 4.5 | 5 | 3.2 |
| 5 | 19 | 19.2 | 10.2 | 6 | 4.3 | 1.7 | 0.7 | 0.7 | 0.7 | 0.3 |
| 6 | 4 | 2.3 | 1 | 0 | 0 | — | — | — | — | — |
| 7 | 4.7 | 1.7 | 1 | 0 | — | — | — | — | — | — |
| 8 | 12 | 12.7 | 8.6 | 5.2 | 3.6 | 0.8 | 0 | — | — | — |
| 9 | 12 | 14.8 | 8.2 | 5.3 | 4.7 | 1.7 | 0.3 | 0 | — | — |
| 10 | 17.2 | 8.2 | 6.5 | 4.8 | 3.3 | 1.7 | 0.7 | 0 | — | — |
| 11 | 17.3 | 10.5 | 7 | 4.7 | 3.7 | 1.3 | 0.7 | 0 | — | — |
| 12 | 15.8 | 13.8 | 9.7 | 8.3 | 5 | 3 | 2.7 | 1 | 0.3 | 0.3 |
| 13 | 17.7 | 12.3 | 10 | 6 | 4 | 2.3 | 2.3 | 2.2 | 0 | — |
| 14 | 12.7 | 2 | 0.7 | 0 | — | — | — | — | — | — |
| 15 | 17.7 | 14.7 | 8.3 | 6.5 | 7.7 | 2.3 | 3.2 | 1.3 | 1.3 | 1.3 |

TABLE 2

Average Irritation Scores (Washed Eyes)

| EXAMPLE | DAYS AFTER TREATMENT | | | | | | | | | |
|---|---|---|---|---|---|---|---|---|---|---|
| | 1 hr | 1 | 2 | 3 | 4 | 7 | 10 | 14 | 17 | 21 |
| 1 | 17.3 | 13.3 | 6.0 | 3.3 | 3.3 | 2.0 | 1.3 | 0.7 | 0.7 | 0.7 |
| 2 | 21 | 17.7 | 13.7 | 11.3 | 8.7 | 4.7 | 4 | 8.7 | 5 | 3.7 |
| 3 | 15 | 10 | 7.3 | 6 | 5.5 | 1.3 | 0.7 | 0 | — | — |
| 4 | 15 | 6.7 | 4 | 2.7 | 2 | 0 | — | — | — | — |
| 5 | 19.7 | 11.7 | 6.7 | 6 | 4.7 | 3.3 | 2 | 1.3 | 0.7 | 0.7 |
| 6 | 11.7 | 4 | 1.3 | 0.7 | 0 | — | — | — | — | — |
| 7 | 5.3 | 1.3 | 1.3 | 0 | — | — | — | — | — | — |
| 8 | 15 | 6.7 | 5.3 | 4.7 | 3.3 | 0.7 | 0 | — | — | — |
| 9 | 12.7 | 12.7 | 9.3 | 6 | 4 | 2 | 0 | — | — | — |
| 10 | 13.3 | 7.3 | 4.7 | 2.7 | 1.3 | 0.7 | 0 | — | — | — |

TABLE 2-continued

Average Irritation Scores (Washed Eyes)

| EXAMPLE | DAYS AFTER TREATMENT | | | | | | | | | |
|---|---|---|---|---|---|---|---|---|---|---|
| | 1 hr | 1 | 2 | 3 | 4 | 7 | 10 | 14 | 17 | 21 |
| 11 | 12.7 | 6.7 | 4.7 | 4.7 | 3.3 | 2 | 0 | — | — | — |
| 12 | 19.7 | 14 | 10 | 8 | 9 | 5.3 | 4 | 3.7 | 2 | 0 |
| 13 | 19 | 11 | 7.7 | 4.7 | 3.3 | 2.1 | 1.3 | 0 | — | — |
| 14 | 9.7 | 0.7 | 0 | 0 | — | — | — | — | — | — |
| 15 | 16.3 | 9.3 | 6.0 | 4.0 | 2.0 | 0.7 | 0 | — | — | — |

The test materials were rated and classified into toxicity categories by the following system:

| Rating | Maximum Average Score | Definition |
|---|---|---|
| Non-Irritating | 0.0–0.5 | To maintain this category, all scores at the 24-hour reading must be zero; otherwise increase category one level. |
| Practically Non-Irritating | Greater than 0.5–2.5 | To maintain this category, all scores at the 24-hour reading must be zero; otherwise increase category one level. |
| Minimally Irritating | Greater than 2.5–15.0 | To maintain this category, all scores at the 72-hour reading must be zero; otherwise increase category one level. |
| Mildly Irritating | Greater than 15.0–25.0 | To maintain this category, scores at the 7-day reading must be zero; otherwise increase category one level. |
| Moderately Irritating | Greater than 25.0–50.0 | To maintain this category, scores at the 7-day reading must be less than or equal to 10 for 60% or more of the animals. Also the 7-day mean score must be less than or equal to 20. If the 7-day mean score is less than or equal to 20, but less than 60% of the animals show scores less than 10, then no animal among those showing scores greater than 10 can exceed a score of 30 if category is to be maintained; otherwise increase category one level. |
| Severely Irritating | Greater than 50.0–80.0 | To maintain this category, scores at the 7-day reading must be less than or equal to 30 for 60% or more of the animals. Also, the 7-day mean score must be less than or equal to 40. If the 7-day mean score is less than or equal to 40, but less than 60% of the animals show scores less than or equal to 30, then no animal among those showing scores greater than 30 can exceed a score of 60 if category is to be maintained; otherwise increase category one level. |

-continued

| Rating | Maximum Average Score | Definition |
|---|---|---|
| Extremely Irritating | Greater than 80.0–110.0 | |

The category of the test material is not to be increased more than one level above its maximum average score.

CLASSIFICATION OF TEST MATERIAL INTO TOXICITY CATEGORIES

| Category | Criteria |
|---|---|
| I | Corrosive (irreversible destruction of ocular tissue) or corneal involvement or conjunctival irritation persisting through Day 21. |
| II | Corneal involvement or conjunctival irritation clearing in 8–21 days. |
| III | Corneal involvement or conjunctival irritation clearing 7 days or less. |
| IV | Minimal effects clearing in less than 24 hours. |

TABLE 3

Test Ratings (Non-Washed Eyes)

| Example | Rating | Toxicity Category |
|---|---|---|
| 1 | Moderately Irritating | I |
| 2 | Moderately Irritating | I |
| 3 | Moderately Irritating | I |
| 4 | Moderately Irritating | I |
| 5 | Mildly Irritating | I |
| 6 | Minimally Irritating | III |
| 7 | Minimally Irritating | III |
| 8 | Mildly Irritating | II |
| 9 | Mildly Irritating | II |
| 10 | Moderately Irritating | II |
| 11 | Moderately Irritating | II |
| 12 | Moderately Irritating | I |
| 13 | Moderately Irritating | II |
| 14 | Minimally Irritating | III |
| 15 | Moderately Irritating | I |

TABLE 4

Test Ratings (Washed Eyes)

| Example | Rating | Toxicity Category |
|---|---|---|
| 1 | Moderately Irritating | I |
| 2 | Moderately Irritating | I |
| 3 | Mildly Irritating | II |
| 4 | Mildly Irritating | III |
| 5 | Mildly Irritating | I |
| 6 | Moderately Irritating | III |
| 7 | Minimally Irritating | III |
| 8 | Mildly Irritating | III |
| 9 | Mildly Irritating | II |
| 10 | Mildly Irritating | II |
| 11 | Mildly Irritating | II |
| 12 | Moderately Irritating | I |
| 13 | Moderately irritating | II |
| 14 | Minimally Irritating | III |
| 15 | Moderately Irritating | II |

Each of the test materials within the scope of the present invention, i.e. Examples 3–15 demonstrate a reduction of the eye irritancy by comparison with compositions of the prior art containing ethoxylated tallowamine but no eye irritation reducing compound, ie. Examples 1 and 2.

In order to determine the efficacy of herbicidal compositions containing a sulfated polyoxyethylene nonylphenol surfactant as an eye initiation reducing agent, the following tests were performed using the isopropylamine salt of glyphosate as the herbicide.

EXAMPLE 16

In this experiment, herbicidal compositions of the present invention were compared with a standard glyphosate composition for herbicidal efficacy. In the tests, material A (standard) was the glyphosate composition containing 15.47 weight percent ethoxylated tallowamine. Materials B, C and D were glyphosate compositions comprising a surfactant composition containing ethoxylated tallowamine (13.1 grams) and sulfated polyoxyethylene nonylphenol (2.3 grams) having 4 moles of ethylene oxide and about 13 weight percent sulfonate as described in Example 9. Material B contained 15.49 weight percent of total surfactant, Material C contained 12.57 weight percent of total surfactant and Material D contained 10.0 weight percent of total surfactant.

The test materials were then diluted with water into 0.5, 1.0, 2.0 and 4.0 weight percent glyphosate aqueous solutions and sprayed onto a test field containing rhizome Johnsongrass. The test plots were evaluated 7 and 14 days after treatment. Percent control of the Johnsongrass is shown in Table 5.

TABLE 5

| | Percent Control | | | | | | | |
|---|---|---|---|---|---|---|---|---|
| | 0.5% | | 1.0% | | 2.0% | | 4.0% | |
| Test Material | 7 days | 14 days | 7 days | 14 days | 7 days | 14 days | 7 days | 14 days |
| A | 42 | 82 | 62 | 99 | 67 | 100 | 88 | 100 |
| B | 57 | 90 | 75 | 99 | 68 | 99 | 88 | 100 |
| C | 42 | 97 | 70 | 99 | 73 | 100 | 88 | 100 |
| D | 47 | 95 | 58 | 99 | 73 | 99 | 83 | 100 |

An untreated check plot showed 0% control of the plants.

EXAMPLE 17

The test materials described in Example 17 were also applied to a test plot containing as its primary vegetation volunteer wheat, yellow foxtail and prickly sida. Also present in the plots were scattered plants of seedling Johnsongrass, velvetleaf and common lambsquarter.

All plots were evaluated 7 and 14 days after treatment. Percent control is shown in Tables 6 and 7.

TABLE 6

Percent Control (7 days after treatment - Average of 3 Plots)

| Test Material | Rate (Pints/Acre) | Volunteer Wheat | Yellow Foxtail | Prickly Sida | Johnson-Grass* | Velvet-Leaf* | Lambs-Quarter* |
|---|---|---|---|---|---|---|---|
| A | 1.0 | 87 | 93 | 72 | 80 | 60 | — |
|   | 1.5 | 95 | 95 | 82 | 90 | 85 | — |
|   | 2.0 | 97 | 98 | 88 | 95 | — | 95 |
| B | 1.0 | 92 | 93 | 73 | 85 | — | — |
|   | 1.5 | 98 | 97 | 88 | 87.5 | — | 95 |
|   | 2.0 | 100 | 100 | 95 | 95 | 90 | — |
| C | 1.0 | 90 | 92 | 82 | 85 | 65 | — |
|   | 1.5 | 97 | 97 | 93 | 92.5 | 80 | — |
|   | 2.0 | 98 | 98 | 93 | 95 | 92.5 | 90 |
| D | 1.0 | 93 | 93 | 90 | — | 60 | — |
|   | 1.5 | 98 | 97 | 90 | 90 | 90 | — |
|   | 2.0 | 100 | 98 | 93 | 95 | 90 | — |

*Insufficient Johnsongrass, Velvetleaf and Lambsquarter plants for complete evaluation.

TABLE 7

Percent Control (14 days after treatment - Average of 3 Plots)

| Test Material | Rate (Pints/Acre) | Volunteer Wheat | Yellow Foxtail | Prickly Sida | Johnson-Grass* | Velvet-Leaf* | Lambs-Quarter* |
|---|---|---|---|---|---|---|---|
| A | 1.0 | 100 | 100 | 95 | 95 | 95 | — |
|   | 1.5 | 100 | 100 | 100 | 100 | 100 | — |
|   | 2.0 | 100 | 100 | 100 | 100 | — | 100 |
| B | 1.0 | 100 | 100 | 98 | 100 | — | — |
|   | 1.5 | 100 | 100 | 100 | 100 | — | 95 |
|   | 2.0 | 100 | 100 | 100 | 100 | 100 | — |
| C | 1.0 | 100 | 100 | 97 | 100 | 80 | — |
|   | 1.5 | 100 | 100 | 98 | — | 80 | — |
|   | 2.0 | 100 | 100 | 100 | 100 | 100 | 100 |
| D | 1.0 | 100 | 100 | 98 | — | 80 | — |
|   | 1.5 | 100 | 100 | 100 | 100 | 100 | — |
|   | 2.0 | 100 | 100 | 100 | 100 | 95 | — |

*Insufficient Johnsongrass, Velvetleaf and Lambsquarter plants for complete evaluation.

The untreated check plot had 0% control of all test plants.

The foregoing herbicidal test results demonstrate that herbicidal compositions containing the surfactant compositions of the present invention maintain or increase the herbicidal activity of herbicidal compositions containing an alkoxylated alkylamine as the only surfactant and provide reduced eye irritation.

In each of the following Examples 18–35, an aqueous solution of the isopropylamine salt of glyphosate containing 62.5 weight percent of such glyphosate salt was used as the herbicidal component and is referred to as "glyphosate solution".

EXAMPLE 18

In this example a herbicidal composition was prepared by mixing glyphosate solution (68.5 grams), water (16.1 grams), and surfactant composition (15.4 grams) to form an aqueous solution. The surfactant composition of this example consisted of 1) ethoxylated tallowamine (13.1 grams) containing about 16–17 moles of ethylene oxide units and about 2–5 weight percent polyethylene glycol (MW=600), and 2) a monohydric phosphate (2.3 grams) from a mixture of alcohols having from 8 to 10 straight chain carbon atoms, no ethylene oxide units, and a phosphomonoester to phosphodiester ratio of 65.5:19.8.

EXAMPLE 19

In this example a herbicidal composition was prepared by mixing glyphosate solution (68.5 grams), water (16.1 grams), and surfactant composition (15.4 grams) to form an aqueous solution. The surfactant composition of this example consisted of 1) ethoxylated tallowamine (12.3 grams) containing from about 16–17 moles of ethylene oxide units and about 2–5 weight percent polyethylene glycol (MW=600), and 2) the monohydric phosphate of Example 18 (3.1 grams).

EXAMPLE 20

In this example a herbicidal composition was prepared by mixing glyphosate solution (68.5 grams), water (16.1 grams), and surfactant composition (15.4 grams) to form an aqueous solution. The surfactant composition consisted of 1) ethoxylated tallowamine (13.1 grams) containing about 16–17 moles of ethylene oxide groups and about 2–5 weight percent polyethylene glycol (MW=600), and 2) a phosphated polyoxyethylene nonylphenol (2.3 grams) having 4 moles of ethylene oxide groups and a phosphomonoester to phosphodiester ratio of 76.4:14.1.

EXAMPLE 21

In this example a herbicidal composition was prepared by mixing glyphosate solution (68.5 grams), water (16.1 grams), and surfactant composition (15.4 grams) to form an aqueous solution. The surfactant composition consisted of 1) ethoxylated tallowamine (11.5 grams) containing about 16–17 moles of ethylene oxide groups and about 2–5 weight percent polyethylene glycol (MW=600), and 2) the phosphated polyoxyethylene nonylphenol of Example 20 (3.9 grams).

EXAMPLE 22

In this example a herbicidal composition was prepared by mixing glyhosate solution (68.5 grams), water (16.1 grams), and surfactant composition (15.4 grams) to form an aqueous solution. The surfactant composition consisted of 1) ethoxylated tallowamine (12.3 grams) containing about 8–13 moles of ethylene oxide groups and about 30 weight percent polyethylene glycol (MW=600), and 2) the phosphated polyoxyethylene nonylphenol of Example 20 (13.1 grams).

EXAMPLE 23

In this example a herbicidal composition was prepared by mixing glyphosate solution (68.5 grams), water (16.1 grams), and surfactant composition (15.4) grams to form an aqueous solution. The surfactant composition consisted of 1) ethoxylated tallowamine (13.1 grams) containing about 8–13 moles of ethylene oxide groups and about 30 weight percent polyethylene glycol (MW=600), and 2) the monohydric phosphate of Example 18 (2.3 grams).

EXAMPLE 24

In this example a herbicidal composition was prepared by mixing glyphosate solution (68.5 grams), water (16.1 grams), polyethylene glycol (MW=400) (5.0 grams), and surfactant composition (10.4 grams) to form an aqueous solution. The surfactant composition consisted of 1) ethoxylated tallowamine (6.2 grams) containing about 8–13 moles of ethylene oxide groups and about 30 weight percent polyethylene glycol (MW=600), and 2) a phosphated polyoxyethylene nonylphenol (4.2 grams) having 4 moles of ethylene oxide groups and a phosphomonoester to phosphodiester ratio of 73.6:11.8.

EXAMPLE 25

In this example a herbicidal composition was prepared by mixing glyphosate solution (68.5 grams), water (16.1 grams), and surfactant composition (15.4 grams) to form an aqueous solution. The surfactant composition consisted of 1) ethoxylated tallowamine (11.6 grams) containing about 8–13 moles of ethylene oxide groups and about 30 weight percent polyethylene glycol (MW=600), and 2) a monohydric phosphate of (3.8 grams) from a mixture of alcohols having from 8 to 10 straight chain carbon atoms, no ethylene oxide units, and a phosphomonoester to phosphodiester ratio of 64.3:20.7.

EXAMPLE 26

In this example a herbicidal composition was prepared by mixing glyphosate solution (68.5 grams), water (16.1 grams), and surfactant composition (15.4 grams) to form an aqueous solution. The surfactant composition consisted of 1) ethoxylated tallowamine (9.2 grams) containing about 16–17 moles of ethylene oxide groups and about 2–5 weight percent polyethylene glycol (MW=600), and 2) the phosphated polyoxyethylene nonylphenol of Example 24 (6.2 grams).

EXAMPLE 27

In this example a herbicidal composition was prepared by mixing glyphosate solution (68.5 grams), water (16.1 grams), polyethylene glycol (MW=400) (5.0 grams), and surfactant composition (10.4 grams) to form an aqueous solution. The surfactant composition consisted of 1) ethoxylated tallowamine (7.8 grams) containing from about 16–17 moles of ethylene oxide groups and about 2–5 weight percent polyethylene glycol (MW=600), and 2) the monohydric phosphate of Example 25 (2.6 grams).

EXAMPLE 28

In this example a herbicidal composition was prepared by mixing glyphosate solution (68.5 grams), water (16.1 grams), polyethylene glycol (MW=400) (5.0 grams), and surfactant composition (10.4 grams) to form an aqueous solution. The surfactant composition consisted of 1) ethoxylated tallowamine (6.2 grams) containing from about 8–13 moles of ethylene oxide groups and about 30 weight percent polyethylene glycol (MW=600), and 2) the phosphated polyoxyethylene nonylphenol of Example 24 (4.2 grams).

EXAMPLE 29

In this example a herbicidal composition was prepared by mixing glyphosate solution (68.5 grams), water (16.1 grams), and surfactant composition (15.4 grams) to form an aqueous solution. The surfactant composition consisted of 1) ethoxylated tallowamine (11.6 grams) containing about 8–13 moles of ethylene oxide groups and about 30 weight percent polyethylene glycol (MW=600), and 2) the monohydric phosphate of Example 25 (3.8 grams).

EXAMPLE 30

In this example a herbicidal composition was prepared by mixing glyphosate solution (68.5 grams), water (16.1 grams), and surfactant composition (15.4 grams) to form an aqueous solution. The surfactant composition consisted of 1) ethoxylated tallowamine (9.2 grams) containing about 15 moles of ethylene oxide groups and about 2–5 weight percent polyethylene glycol (MW-600), and 2) the phosphated polyoxyethylene nonylphenol of Example 24 (6.2 grams).

EXAMPLE 31

In this example a herbicidal composition was prepared by mixing glyphosate solution (68.5 grams), water (16.1 grams), polyethylene glycol (MW=400) (5.0 grams), and surfactant composition (10.4 grams) to form an aqueous solution. The surfactant composition consisted of 1) ethoxylated tallowamine (7.8 grams) containing about 15 moles of ethylene oxide groups and about 2–5 weight percent polyethylene glycol (MW=600), and 2) the monohydric phosphate of Example 25 (2.6 grams).

In Table 8 which follows data are provided showing the average eye irritation scores of six rabbits exposed in individual tests without washing to each of the compositions in Examples 18–31.

TABLE 8

Average Irritation Scores (Non-Washed Eyes)

| EXAMPLE | 1 hr | 1 | 2 | 3 | 4 | 7 | 10 | 14 | 17 | 21 |
|---|---|---|---|---|---|---|---|---|---|---|
| 18 | 11.3 | 12 | 12.2 | 17.3 | 14.8 | 16.3 | 15.8 | 16.3 | 15.3 | 7.8 |
| 19 | 9.3 | 9.7 | 13.7 | 16.0 | 16.8 | 19.7 | 21.8 | 17.7 | 19.8 | 13.3 |
| 20 | 8.3 | 9.3 | 13.5 | 10.7 | 8.6 | 11.8 | 12.8 | 10.5 | 9.5 | 6.3 |
| 21 | 9.3 | 10.8 | 13.7 | 13.8 | 13.5 | 15.8 | 13.2 | 11.5 | 8.0 | 5.0 |
| 22 | 18.5 | 14.8 | 11.3 | 7.3 | 6.5 | 4.3 | 2.8 | 1.8 | 1.5 | 1.5 |
| 23 | 20.8 | 19.0 | 16.2 | 19.3 | 12.7 | 8.3 | 6.3 | 5.0 | 4.7 | 8.0 |
| 24 | 11.0 | 6.7 | 4.7 | 2.3 | 0.3 | 0.3 | 0 | — | — | — |
| 25 | 14.0 | 10.0 | 8.5 | 4.3 | 2.0 | 1.3 | 0 | — | — | — |
| 26 | 11.3 | 11.2 | 9.2 | 8.8 | 8.2 | 2.2 | 1.0 | 0 | — | — |
| 27 | 12.8 | 11.7 | 10.3 | 8.0 | 7.3 | 3.8 | 3.2 | 2.0 | 2.3 | 2.0 |
| 28 | 11.7 | 7.3 | 5.0 | 3.0 | 3.0 | 1.0 | 0 | — | — | — |
| 29 | 14.8 | 12.5 | 11.3 | 9.0 | 7.2 | 1.5 | 0 | — | — | — |
| 30 | 11.5 | 9.8 | 4.7 | 3.0 | 2.7 | 0.7 | 0 | — | — | — |
| 31 | 12.2 | 11.3 | 9.8 | 7.5 | 6.3 | 2.2 | 1.2 | 1.2 | 1.2 | 0 |

EXAMPLE 32

In this example of prior art a herbicidal composition was prepared by mixing glyphosate solution (68.5 grams), water (21.5 grams), and surfactant composition (10.0 grams) to form an aqueous solution. The surfactant composition consisted of 1) ethoxylated tallowamine (7.2 grams) containing about 15 moles of ethylene oxide groups, and 2) additional polyethylene glycol (MW=600), ethylene glycol, and water to total 2.8 grams. The resulting composition was tested for eye irritation as above and gave results placing it in Toxicity Category I.

EXAMPLE 33

In this example of the present invention a herbicidal composition was prepared by mixing glyphosate solution (68.5 grams), water (18.2 grams), and surfactant composition (13.3 grams) to form an aqueous solution. The surfactant composition consisted of 1) ethoxylated tallowamine (7.2 grams) containing about 15 moles of ethylene oxide groups, 2) the phosphated polyoxyethylene nonylphenol of Example 20 (3.0 grams) and 3) additional polyethylene glycol (MW=600) and dipropylene glycol to total 3.1 grams. The resulting composition was tested for eye irritation as above and gave results placing it in Toxicity Category III.

EXAMPLE 34

In this example of prior art a herbicidal composition was prepared by mixing glyphosate solution (68.5 grams), water (16.1 grams), and surfactant composition (15.4 grams) to form an aqueous solution. The surfactant composition consisted of 1) ethoxylated tallowamine (11.0 grams) containing about 15 moles of ethylene oxide groups, and 2) additional polyethylene glycol (MW=600), ethylene glycol, and water to total 4.4 grams. The resulting composition was tested for eye irritation as above and gave results placing it in Toxicity Category I.

EXAMPLE 35

In this example of the present invention a herbicidal composition was prepared by mixing glyphosate solution (68.5 grams), water (2.5 grams), and surfactant composition (29.0 grams) to fore an aqueous solution. The surfactant composition consisted of 1) ethoxylated tallowamine (11.0 grams) containing about 15 moles of ethylene oxide groups,
2) the phosphated polyoxyethylene nonylphenol of Example 20 (3.6 grams), and 3) additional polyethylene glycol (MW=600), propylene glycol, and dipropylene glycol to total 14.4 grams. The resulting composition was tested for eye irritation as above and gave results placing it in Toxicity Category II.

It should be understood that embodiments of the present invention have been described as merely illustrative of a few of the applications of the principles of the present invention. Numerous modifications may be made by those skill in the art without departing from the spirit and scope of the invention.

What is claimed is:

1. A composition which is an aqueous solution comprising:

(a) a glyphosate herbicide in a herbicidally effective amount, (b) an amine surfactant component having the chemical structure

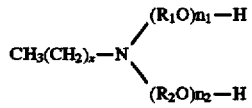

wherein x is a number from about 7 to about 19; $n_1$ and $n_2$ are numbers independently selected from 1 to about 30; the average sum of $n_1$ and $n_2$ is 2 or greater; $R_1$ and $R_2$ are C2–C4 alkylene radicals, said amine surfactant being in an amount sufficient to potentiate the glyphosate herbicidal activity but at the same time sufficient to cause unacceptable eye irritation; and (c) an effective eye irritation reducing amount of a phosphate monoester or mixture of phosphate monoesters having the general formula

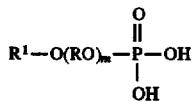

wherein $R^1$ is $C_8$–$C_{20}$ alkyl or $C_8$–$C_{20}$ alkylphenyl; R is $C_2$–$C_4$ alkylene: m is zero or a number up to about 60; alone or in combination with a phosphate diester or mixture of phosphate diesters having the general formula;

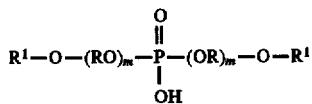

wherein R, $R_1$, and m are as just described, provided the weight percentage of phosphate monoester (on monoesters) exceeds that of the phosphate diester (or diesters).

2. The composition of claim 1 wherein $R^1$ is nonylphenyl and m is about 4.

3. The composition of claim 1 wherein $R^1$ is $C_8$–$C_{10}$ straight chain alkyl and m is 0.

4. The composition of claim 1, 2, or 3 wherein in the anime surfactant component $R_1$ and $R_2$ are each ethylene and the average sum of m, and $n_2$ is from about 4 to about 20.

5. The composition of claim 4 wherein the amine surfactant component comprises ethoxylated tallow anime having 8–13 moles of ethylene oxide.

6. The composition of claim 1 wherein (b) and (c) are present in a weight/weight ratio of about 80:20 to about 85:15.

7. The composition of claim 1 wherein the weight/weight ratio of glyphosate herbicide, expressed as acid equivalent, to the total of components (b) and (c) is in the range of 1:1 to 5:1.

8. In an aqueous herbicidal solution of a glyphosate herbicide potentiated with a polyoxyalkylene alkylamine surfactant having the chemical structure

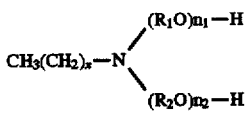

wherein x is a number from about 7 to about 19; $n_1$ and $n_2$ are numbers independently selected from 1 to about 30; the average sum of $n_1$ and $n_2$ is 2 or greater; and $R_1$ and $R_2$ are $C_2$–$C_4$ alkylene radicals, the improvement characterized by having incorporated in the solution an amount effective to appreciably reduce the eye irritation of the solution of a phosphate monoester or diester surfactant or a mixture thereof having the general formula

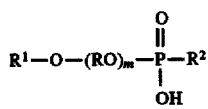

wherein $R^1$ is $C_8$–$C_{20}$ alkyl or $C_8$–$C_{20}$ alkylphenyl; R is $C_2$–$C_4$ alkylene radical, ethylene or propylene; m is zero or a number up to about 60; and $R^2$ is hydroxyl or the $R^1$—O—(RO)$_m$ radical wherein R, $R^1$ and m are as just described, wherein the weight percentage of phosphate monoester surfactant equals or exceeds that of phosphate diester surfactant.

9. A method of controlling vegetation comprising spraying on the foliage of the vegetation a herbicidally effective amount of the composition of claim 8.

* * * * *

UNITED STATES PATENT AND TRADEMARK OFFICE
CERTIFICATE OF CORRECTION

| | | |
|---|---|---|
| PATENT NO. | : | 5,703,015 |
| DATED | : | December 30, 1997 |
| INVENTOR(S) | : | Paul D. Berger and Antonio M. Jimenez |

It is certified that error appears in the above-identified patent and that said Letters Patent is hereby corrected as shown below:

In claim 1, column 25, line 10, please delete "on" and insert therefor --or--.

In claim 4, column 25, line 18, please delete "anime" and insert therefor --amine--.

In claim 5, column 25, line 22, please delete "anime" and insert therefor --amine--.

Signed and Sealed this

Seventh Day of April, 1998

Attest:

BRUCE LEHMAN

Attesting Officer

Commissioner of Patents and Trademarks